(12) United States Patent
Nord et al.

(10) Patent No.: US 7,831,018 B1
(45) Date of Patent: Nov. 9, 2010

(54) METHOD AND APPARATUS TO FACILITATE OPTIMIZING A RADIATION-TREATMENT LEAF-SEQUENCE PLAN

(75) Inventors: Janne Nord, Espoo (FI); Jarkko Peltola, Tuusula (FI)

(73) Assignee: Varian Medical Systems International AG (CH)

( * ) Notice: Subject to any disclaimer, the term of this patent is extended or adjusted under 35 U.S.C. 154(b) by 55 days.

(21) Appl. No.: 12/478,394

(22) Filed: Jun. 4, 2009

(51) Int. Cl.
*A61N 5/10* (2006.01)
(52) U.S. Cl. ....................................................... 378/65
(58) Field of Classification Search .................... 378/65
See application file for complete search history.

(56) References Cited

U.S. PATENT DOCUMENTS

| | | |
|---|---|---|
| 7,162,008 B2 | 1/2007 | Earl et al. |
| 7,333,591 B2 | 2/2008 | Earl et al. |
| 2006/0256915 A1 | 11/2006 | Otto et al. |
| 2008/0144772 A1 | 6/2008 | Yi et al. |
| 2008/0226030 A1 | 9/2008 | Otto |
| 2008/0298550 A1 | 12/2008 | Otto |

FOREIGN PATENT DOCUMENTS

| | | |
|---|---|---|
| WO | 2008011725 A1 | 1/2008 |
| WO | 2008130634 A1 | 10/2008 |

OTHER PUBLICATIONS

Yi et al., "A Dose Rate Modulated Tracking Radiation Therapy System and Method," U.S. Appl. No. 60/874,678; filed Dec. 14, 2006; 23 pages.
Wang et al., "Arc-Modulated Radiation Therapy (AMRT): A Single Arc Form of Intensity-Modulated Arc Therapy," Physics in Medicine and Biology 53 (2008); 13 pages; IOP Publishing.

*Primary Examiner*—Courtney Thomas
(74) *Attorney, Agent, or Firm*—Fitch, Even, Tabin & Flannery

(57) ABSTRACT

These teachings provide for identifying (101) a set of fluence-based control points to represent a leaf sequence and then selecting (102) a first subset of the fluence-based control points and optimizing that first subset. This first subset (now optimized) is combined (103) with a second subset of the fluence-based control points and the aggregation then optimized. The latter activities are then iteratively repeated (104) with additional subsets of the fluence-based control points to provide resultant optimized sets of fluence-based control points. This eventually results in a fully optimized complete set of fluence-based control points. This optimized set of fluence-based control points are then used (105) to specify a corresponding radiation-treatment leaf-sequence plan.

14 Claims, 1 Drawing Sheet

METHOD AND APPARATUS TO FACILITATE OPTIMIZING A RADIATION-TREATMENT LEAF-SEQUENCE PLAN

TECHNICAL FIELD

This invention relates generally to the optimization of radiation-treatment leaf-sequence plans and more particularly to optimization using fluence-based control points.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not discriminate between unwanted materials and adjacent tissues, organs, or the like that are desired or even critical to continued survival of the patient. As a result, radiation is ordinarily applied in a carefully administered manner to at least attempt to restrict the radiation to a given target volume.

Collimators are often used to restrict and form the radiation-therapy beam. Many collimators have a fixed aperture. Other collimators have an aperture that can be adjusted in one or more dimension. Adjustable apertures permit, to at least some degree, customization of the radiation-therapy beam's cross section to thereby attempt to better match the requirements of a given target volume. Multileaf collimators are an example of such a component. Multileaf collimators are comprised of a plurality of individual parts (known as "leaves") that are formed of a high atomic numbered material (such as tungsten) that can move independently in and out of the path of the radiation-therapy beam in order to selectively block (and hence shape) the beam.

Many treatment plans provide for exposing the target volume to radiation from a number of different directions. Arc therapy, for example, comprises one such approach. In such a case it often becomes useful or necessary to adjust the multileaf collimator to accommodate various differences that occur or accrue when moving the radiation source with respect to the target volume. A radiation-treatment leaf-sequence plan provides information regarding useful or necessary adjustments to the multileaf collimator(s) during such a treatment.

Optimizing such a plan can prove challenging. By one approach, fluence-based control points are utilized to optimize the plan. The number of such control points can be considerable, however, and even fast optimizers can be challenged to provide timely results. When the overall plan includes a large number of individual leaf-settings, the overall computational challenge can be considerable. In some application settings, this time requirement can result in vexing delays. These delays, in turn, can lead to expensive and undesirable equipment downtime, patient discomfort, and increased costs.

BRIEF DESCRIPTION OF THE DRAWINGS

The above needs are at least partially met through provision of the method and apparatus to facilitate optimizing a radiation-treatment leaf-sequence plan described in the following detailed description, particularly when studied in conjunction with the drawings, wherein.

Figure 1:
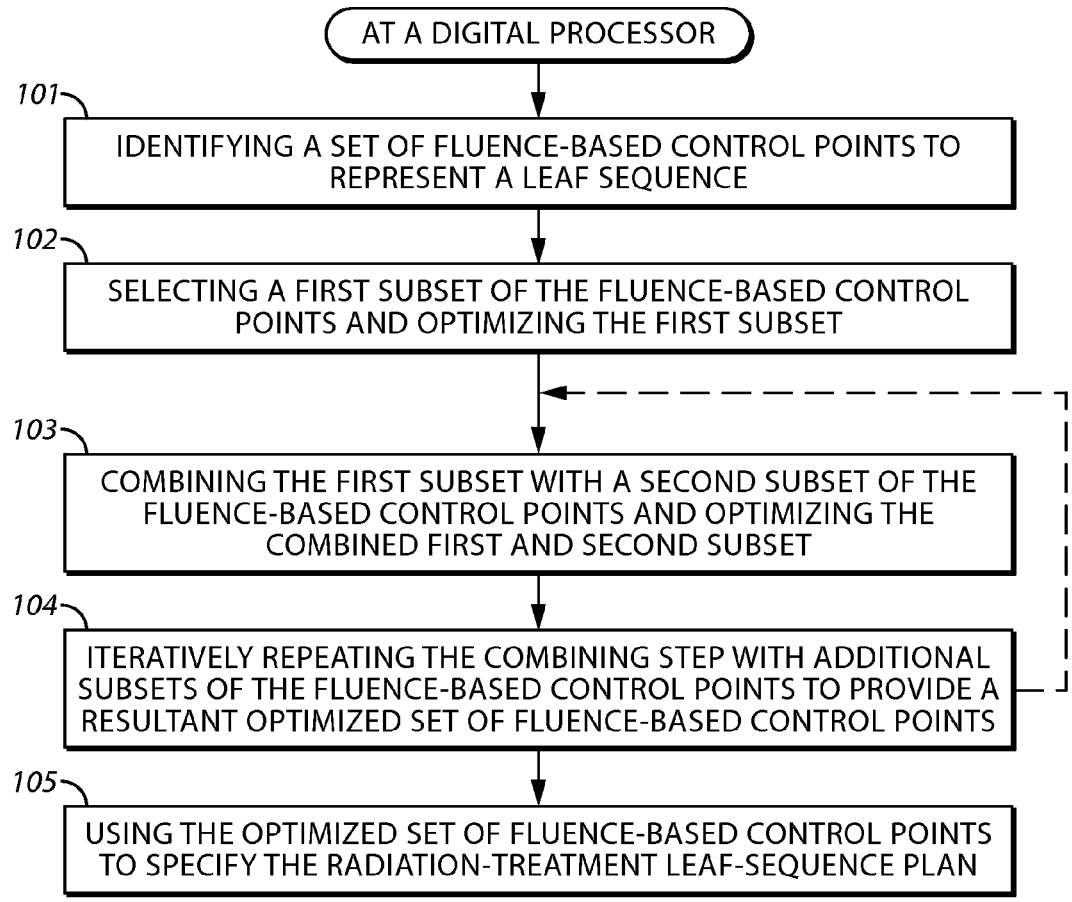
FIG. 1 comprises a flow diagram as configured in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these various embodiments are suitable for use in optimizing a radiation-treatment leaf-sequence plan and can be carried out by a corresponding digital processor. These teachings provide for identifying a set of fluence-based control points to represent a leaf sequence and then selecting a first subset of the fluence-based control points and optimizing that first subset. This first subset (now optimized) is combined with a second subset of the fluence-based control points and the aggregation then optimized. The latter steps are then iteratively repeated with additional subsets of the fluence-based control points to provide resultant optimized sets of fluence-based control points. This eventually results in a fully optimized complete set of fluence-based control points. This optimized set of fluence-based control points are then used to specify a corresponding radiation-treatment leaf-sequence plan.

By one approach, none of these subsets overlap with one another. The aforementioned optimization can be carried out in any of a variety of ways. By one approach this can comprise using steepest descent-based optimization. By another approach and as another example, this can comprise using simulated annealing-based optimization.

So configured, these teachings yield optimized results faster, and in some cases considerably faster, than processes that optimize by processing all of the fluence-based control points in a single optimization step/process. This speed can be leveraged in various ways depending upon the application setting. By one approach, for example, these teachings are acceptable for use in an on-the-fly application setting.

Those skilled in the art will further appreciate that these teachings are highly scalable. For example, the described approaches are successfully usable in application settings that employ a large number of fluence-based control points as well as application settings that employ only a relatively small number of fluence-based control points. These teachings are also easily employed with a variety of optimization techniques and hence serve to greatly leverage numerous existing approaches in these regards.

These and other benefits may become clearer upon making a thorough review and study of the following detailed description. Referring now to the drawings, and in particular to FIG. 1, an illustrative process 100 that is compatible with many of these teachings will now be presented. This process 100 can be carried out by a digital processor of choice with certain examples being provided below where appropriate.

This process 100 includes the step 101 of identifying a set of fluence-based control points to represent a leaf sequence. As used herein, the expression "fluence" will be understood to refer to radiative flux integrated over time and in particular to the number of particles that intersect a given unit area. Fluence values are well known in the art and describe the strength of a radiation field. These values comprise one of the fundamental metrics in dosimetry.

The aforementioned leaf sequence, as noted earlier, will typically correspond to leaf configurations for each of a plurality of treatment segments as comprise a given radiation-treatment leaf-sequence plan. These teachings are applicable with a number of multi-segment treatment approaches including, but not limited to, arc-therapy treatment approaches and the like. For the sake of illustration and not by way of limitation, there may be, for example, one hundred such fluence-based control points for each such treatment segment.

This process 100 includes the step 102 of selecting a first subset of the fluence-based control points and optimizing that first subset. This first subset might comprise, for example (and without intending any limitations in these regards), five of the fluence-based control points. By one approach these control points can be selected largely, or wholly, at random. By another approach these control points can be selected using a predetermined selection criterion (or criteria). For example, it may be useful in some application settings to select one such control point from each of a corresponding plurality of segregated regions.

The aforementioned optimization can be carried out using an optimization approach of choice. By one approach, for example, this can comprise using steepest descent-based optimization. Steepest descent-based optimization (sometimes also referred to as gradient descent-based optimization) comprises a first-order optimization algorithm. Generally speaking, to find a local minimum of a function using this approach one takes steps proportional to the negative of the gradient (or some corresponding approximation) of the function at the current point. By another approach, and as another non-limiting example, the referred-to optimization can comprise using simulated annealing-based optimization. Simulated annealing comprises a probabilistic metaheuristic to locate a good approximation to the global minimum of a given function in a typically large search space. Such techniques are well known and require no further description here.

This process 100 then provides the step 103 of combining the optimized first subset with a second subset of the fluence-based control points and then optimizing that combination of the first and second subset. The number of control points in the second subset can be the same as the number of control points in the optimized first subset or can be fewer in number or more. The optimization of this combination of the first and second subsets can use the same optimization technique as was applied earlier when optimizing the first subset of fluence-based control points or, if desired, a partially or wholly different optimization technique. Those skilled in the art will recognize and understand that this step of optimizing the combination of the first subset with the second subset can and will often result in yielding new values for at least some of the fluence-based control points of the optimized first subset. This is an expected and even a desirable occurrence.

Step 104 serves to represent then iteratively repeating the aforementioned combining step with additional subsets of the fluence-based control points to eventually provide a resultant optimized set of fluence-based control points that accounts for and represents all of the fluence-based control points as serve to represent the leaf sequence. As one simple illustrative example in these regards, when the total number of fluence-based control points equals one hundred and each subset has five control points, this process 100 will provide for combining twenty such subsets in order to ultimately optimize all one hundred control points.

So configured, this process 100 can be viewed as initially representing the leaf sequence as only a very coarse set of control points. This very coarse set of control points is optimized to produce as accurate a fluence as possible. Once this coarse solution has converged, this process moves to a somewhat less-coarse representation by adding a few more control points. This optimize-then-add-control-points approach then cycles repeatedly to produce a series of increasingly accurate representations until finally the process accounts for all of the control points.

In step 105 this optimized set of fluence-based control points is used to specify a corresponding radiation-treatment leaf-sequence plan. This step can comprise conventional practice in these regards if desired. Accordingly, for the sake of brevity and clarity, further elaboration in these regards will not be provided here regarding this step.

Figure 2:
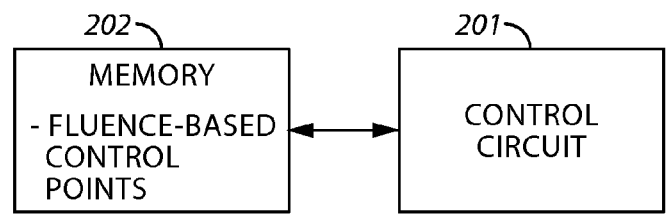
FIG. 2 comprises a block diagram as configured in accordance with various embodiments of the invention.

Those skilled in the art will appreciate that the above-described processes are readily enabled using any of a wide variety of available and/or readily configured platforms, including partially or wholly programmable platforms as are known in the art or dedicated purpose platforms as may be desired for some applications. Referring now to FIG. 2, an illustrative approach to such a platform will now be provided.

In this illustrative example, the digital processor apparatus comprises a radiation-treatment leaf-sequence plan optimizer 200 having a control circuit 201 that operably couples to a memory 202. This memory 202 can have a set of fluence-based control points that represent a leaf sequence (for example, as described above) stored therein. It will be understood that the memory component shown can comprise a plurality of memory elements or can comprise a single memory element (as is suggested by the illustration). This memory 202 can also contain, as desired, digital computer operating instructions to carry out one or more of the steps, actions, or functions described herein.

Those skilled in the art will also recognize and appreciate that the control circuit 201 can comprise a fixed-purpose hard-wired platform or can comprise a partially or wholly programmable platform. All of these architectural options are well known and understood in the art and require no further description here.

This control circuit 201 can be configured (using, for example, programming as will be well understood by those skilled in the art) to carry out one or more of the steps, actions, and/or functions described herein. This can comprise, for example, configuring the control circuit 201 to identify a set of fluence-based control points that represent a leaf sequence to accommodate each of a plurality of treatment segments as pertain to a given radiation-treatment leaf-sequence plan and to then select a first subset of the fluence-based control points and optimize that first subset. This can also comprise configuring the control circuit 201 to combine the optimized first subset with a second subset of the fluence-based control points (that are different than the fluence-based control points that comprise the first subset) and to then optimize those combined subsets. This control circuit 201 can then iteratively repeat this combining step with additional non-overlapping subsets of the fluence-based control points to finally provide a resultant optimized set of fluence-based control points to thereby permit use of that result to specify the desired radiation-treatment leaf-sequence plan.

Those skilled in the art will recognize and understand that such an apparatus 200 may be comprised of a plurality of physically distinct elements as is suggested by the illustration shown in FIG. 2. It is also possible, however, to view this illustration as comprising a logical view, in which case one or more of these elements can be enabled and realized via a shared platform. It will also be understood that such a shared platform may comprise a wholly or at least partially programmable platform as are known in the art.

So configured, these teachings permit the determination of an optimized set of fluence-based control points that is every bit as accurate as prior art approaches would yield albeit in a considerably less amount of time. For example, in an application setting where prior approaches might consume upwards of 200 ms to yield an optimized set of fluence-based control points, these teachings will likely consume only about 10 ms. This, in turn, makes these teachings useful in a wider variety of application settings.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method to facilitate optimizing a radiation-treatment leaf-sequence plan, comprising:
   at a digital processor:
   identifying a set of fluence-based control points to represent a leaf sequence;
   selecting a first subset of the fluence-based control points and optimizing the first subset to provide an optimized first subset;
   combining the optimized first subset with a second subset of the fluence-based control points and optimizing the combined first and second subset;
   iteratively repeating the combining step with additional subsets of the fluence-based control points to provide a resultant optimized set of fluence-based control points;
   using the optimized set of fluence-based control points to specify the radiation-treatment leaf-sequence plan.

2. The method of claim 1 wherein none of the subsets of the fluence-based control points overlap with one another.

3. The method of claim 1 wherein the radiation-treatment leaf-sequence plan comprises a plurality of treatment segments and wherein the leaf sequence comprises a corresponding leaf configuration for each of the segments.

4. The method of claim 1 wherein optimizing comprises using steepest descent-based optimization.

5. The method of claim 1 wherein optimizing comprising using simulated annealing-based optimization.

6. A radiation-treatment leaf-sequence plan optimizer comprising:
   a memory having stored therein a set of fluence-based control points that represent a leaf sequence;
   a control circuit operably coupled to the memory and being configured to:
   select a first subset of the fluence-based control points and optimize the first subset to provide an optimized first subset;
   combine the optimized first subset with a second subset of the fluence-based control points and optimize the combined first and second subset;
   iteratively repeat the combining step with additional subsets of the fluence-based control points to provide a resultant optimized set of fluence-based control points;
   use the optimized set of fluence-based control points to specify the radiation-treatment leaf-sequence plan.

7. The radiation-treatment leaf-sequence plan optimizer of claim 6 wherein none of the subsets of the fluence-based control points overlap with one another.

8. The radiation-treatment leaf-sequence plan optimizer of claim 6 wherein the radiation-treatment leaf-sequence plan comprises a plurality of treatment segments and wherein the leaf sequence comprises a corresponding leaf configuration for each of the segments.

9. The radiation-treatment leaf-sequence plan optimizer of claim 6 wherein the control circuit is configured to optimize by using steepest descent-based optimization.

10. The radiation-treatment leaf-sequence plan optimizer of claim 6 wherein the control circuit is configured to optimize by using simulated annealing-based optimization.

11. A method to facilitate optimizing a radiation-treatment leaf-sequence plan that includes a plurality of treatment segments, comprising:
    at a digital processor:
    identifying a set of fluence-based control points to represent a leaf sequence to accommodate each of the treatment segments;
    selecting a first subset of the fluence-based control points and optimizing the first subset to provide an optimized first subset;
    combining the optimized first subset with a second subset of the fluence-based control points that are different than the fluence-based control points that comprise the first subset and optimizing the combined first and second subset;
    iteratively repeating the combining step with additional non-overlapping subsets of the fluence-based control points to provide a resultant optimized set of fluence-based control points;
    using the optimized set of fluence-based control points to specify the radiation-treatment leaf-sequence plan.

12. The method of claim 11 wherein the radiation-treatment leaf-sequence plan comprises a radiation-treatment leaf-sequence plan for an arc therapy treatment.

13. The method of claim 11 wherein optimizing comprises using steepest descent-based optimization.

14. The method of claim 11 wherein optimizing comprising using simulated annealing-based optimization.

* * * * *